US 10,947,343 B2

(12) United States Patent
Yoshioka et al.

(10) Patent No.: US 10,947,343 B2
(45) Date of Patent: Mar. 16, 2021

(54) PRODUCTION METHOD OF POLYOXYETHYLENE DERIVATIVE HAVING PLURALITY OF HYDROXYL GROUPS AT TERMINAL

(71) Applicant: NOF CORPORATION, Tokyo (JP)

(72) Inventors: Hiroki Yoshioka, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 16/492,883

(22) PCT Filed: Mar. 22, 2018

(86) PCT No.: PCT/JP2018/011497
§ 371 (c)(1),
(2) Date: Sep. 10, 2019

(87) PCT Pub. No.: WO2018/180917
PCT Pub. Date: Oct. 4, 2018

(65) Prior Publication Data
US 2020/0079903 A1    Mar. 12, 2020

(30) Foreign Application Priority Data
Mar. 31, 2017 (JP) .............................. JP2017-069699

(51) Int. Cl.
*C08G 65/26* (2006.01)
*C08G 65/331* (2006.01)
*A61K 47/60* (2017.01)

(52) U.S. Cl.
CPC ..... *C08G 65/2606* (2013.01); *C08G 65/3312* (2013.01); *A61K 47/60* (2017.08)

(58) Field of Classification Search
CPC ............ C08G 65/2606; C08G 65/3322; C08G 65/322; C08G 65/325; C08G 65/3312; C08G 65/48; C08G 2650/42; C08G 2650/50; A61K 47/60; A61K 47/10; C08K 5/053
See application file for complete search history.

(56) References Cited

U.S. PATENT DOCUMENTS

| | | | |
|---|---|---|---|
| 3,721,682 A | 3/1973 | Murai et al. | |
| 4,474,596 A | 10/1984 | Kruger et al. | |
| 4,562,265 A * | 12/1985 | Machell ............... | C07D 317/20 549/364 |
| 2010/0261863 A1 | 10/2010 | Takehana et al. | |
| 2012/0322955 A1 | 12/2012 | Yoshioka et al. | |

FOREIGN PATENT DOCUMENTS

| | | |
|---|---|---|
| EP | 2 692 771 A1 | 2/2014 |
| JP | 48-43748 B1 | 12/1973 |
| JP | 57-200381 A | 12/1982 |
| JP | 2-231488 A | 9/1990 |
| JP | 2011-157466 A | 8/2011 |
| JP | 2012-214747 A | 11/2012 |
| WO | 2010/114074 A1 | 10/2010 |
| WO | 2012/133490 A1 | 10/2012 |

OTHER PUBLICATIONS

International Search Report (PCT/ISA/210) dated Jun. 5, 2018 issued by the International Searching Authority in International Application No. PCT/JP2018/011497.
Written Opinion (PCT/ISA/237) dated Jun. 5, 2018 issued in International Application No. PCT/JP2018/011497.
Arthur T. Ness et al., "New Derivatives of 2,3,4,5-Dibenzylidene-D,L-xylitol and 2,4:3,5-Dimethylene-L-xylitol", Chem. Soc., vol. 75, 1953, pp. 132-134.
Jonathan Clayden et al. "Saturated heterocycles and stereoelectronics" Organic Chemistry, Oxford university Press, Jan. 1, 2001 (pp. 1137-1138).
Communication dated Dec. 18, 2020, from the European Patent Office in counterpart European Application No. 18774311.7.

* cited by examiner

*Primary Examiner* — Shane Fang
(74) *Attorney, Agent, or Firm* — Sughrue Mion, PLLC

(57) ABSTRACT

A method of producing a polyoxyethylene derivative (1):

$$X-L^1-(OCH_2CH_2)_n-O-CH_2 \atop \begin{pmatrix} HC-OH \\ | \\ HC-OH \end{pmatrix}_a \atop HC-OH \atop H_2C-OH \quad (1)$$

where L1 is a divalent linker, X is a functional group capable of reacting with a physiologically active substance, a is 1 or 2, and n is from 11 to 3,650. The method includes Step (A): protecting 4 or 6 hydroxyl groups in a polyhydric alcohol having 5 or 7 hydroxyl groups by cyclic benzylidene acetalization to obtain a compound having a hydroxyl group at a 1-position and a protective group of a cyclic benzylidene acetal structure; Step (B): polymerizing from 11 to 3,650 moles of ethylene oxide to the compound obtained in the step (A) to obtain a polyoxyethylene derivative; Step (C): converting the hydroxyl group at a terminal of the polyoxyethylene derivative to a functional group capable of reacting with a physiologically active substance; and Step (D): deprotecting the protective group of the polyoxyethylene derivative.

6 Claims, No Drawings

PRODUCTION METHOD OF POLYOXYETHYLENE DERIVATIVE HAVING PLURALITY OF HYDROXYL GROUPS AT TERMINAL

CROSS REFERENCE TO RELATED APPLICATIONS

This application is a National Stage of International Application No. PCT/JP2018/011497 filed Mar. 22, 2018, claiming priority based on Japanese Patent Application No. 2017-069699 filed Mar. 31, 2017.

TECHNICAL FIELD

The present invention relates to a production method of a polyoxyethylene derivative having a plurality of hydroxyl groups at a terminal, which is used in application for modifying a physiologically active substance.

BACKGROUND ART

When a physiologically active substance, for example, hormone, cytokine or enzyme is administered to a living body, it is discharged from the living body by glomerular filtration in the kidney and the uptake by macrophage in the liver, spleen or the like. Therefore, it has a short half-life in blood and hence it is difficult to obtain a sufficient pharmacological effect. In order to solve the problem, it has been attempted to chemically modify the physiologically active substance with an amphipathic polymer, for example, a sugar chain or polyoxyethylene, or albumin. By these attempts, the behavior of the physiologically active substance in a living body is improved due to increase in the molecular weight, formation of a hydration layer or the like. Further, it is also known that the effect, for example, decrease in toxicity or antigenicity is obtained by the modification with polyoxyethylene.

As to the physiologically active substances modified with polyoxyethylene, ten or more thereof have been approved as pharmaceuticals by FDA or the like, and the effectiveness of the modification with polyoxyethylene is well known. Even now, a lot of developments on the physiologically active substances modified with polyoxyethylene have been made, and it has been desired to develop a polyoxyethylene derivative having a new added value.

As the polyoxyethylene derivative having a new added value, in Patent Document 1 there is description relating to a polyoxyethylene derivative having a plurality of hydroxyl groups at a terminal. Since the polyoxyethylene derivative has a plurality of hydroxyl groups at a terminal, a strong and large hydration layer is formed around the drug modified. It is described that as a result, the interaction with opsonin is decreased to reduce antigenicity. However, according to the production method of the polyoxyethylene derivative described in the patent document, since hydroxyl groups of a polyhydric alcohol, for example, xylitol or volemitol are protected by isopropylidene acetalization, isomers are by-produced and in order to remove them, a multi-stage purification process is required so that the yield is significantly decreased. Therefore, further improvement is needed in terms of industrial production.

In Non-Patent Document 1, there is description relating to protection of xylitol with benzylidene acetalization. In the protection of xylitol with benzylidene acetalization, the isomers generated in the isopropylidene acetalization are not by-produced and while leaving a hydroxyl group at a 1-position, other hydroxyl groups can be protected.

PRIOR ART DOCUMENT

Patent Document

Patent Document 1: JP-A-2012-214747

Non-Patent Document

Non-Patent Document 1: Arthur T. Ness, Raymond M. Hann, C. S. Hudson, J. Am. Chem., 75, 132-134 (1953)

SUMMARY OF INVENTION

Problems to be Solved by the Invention

However, in Non-Patent Document 1 only the protection of xylitol is described and there is no description relating to a reaction so as to synthesize a polyoxyethylene derivative using the protected product as a raw material. Moreover, since solubility of the benzylidene-acetalized xylitol is extremely low and the benzylidene-acetalized xylitol is almost insoluble in water and an organic solvent, it is very difficult to efficiently convert a hydroxyl group at a 1-position in a reaction.

An object of the invention is to provide a production method which can produce a high purity polyoxyethylene derivative having a plurality of hydroxyl groups at a terminal which is suitable for pharmaceutical use in an industrially high yield.

Means for Solving the Problems

As a result of the intensive investigations to solve the problem described above, the inventors have established a production method of a polyoxyethylene derivative having a plurality of hydroxyl groups at a terminal, which is composed of the constitution described below.

Thus, the present invention is as follows.

[1] A production method of a polyoxyethylene derivative represented by formula (1) shown below which comprises performing step (A), step (B), step (C) and step (D) described below:

$$X-L^1-(OCH_2CH_2)_n-O-CH_2 \atop \begin{pmatrix} HC-OH \\ HC-OH \end{pmatrix}_a \atop HC-OH \atop H_2C-OH \quad (1)$$

(in formula (1), $L^1$ is a divalent linker, X is a functional group capable of reacting with a physiologically active substance, a is 1 or 2, and n is from 11 to 3,650.);

Step (A): a step wherein in a polyhydric alcohol having 5 or 7 hydroxyl groups, 4 or 6 of the hydroxyl groups are protected by cyclic benzylidene acetalization to obtain a compound having the hydroxyl group at a 1-position and a protective group of a cyclic benzylidene acetal structure;

Step (B): a step wherein from 11 to 3,650 moles of ethylene oxide are polymerized to the compound obtained in the step (A) to obtain a polyoxyethylene derivative;

Step (C): a step wherein the hydroxyl group at a terminal of the polyoxyethylene derivative obtained in the step (B) is converted to the functional group capable of reacting with a physiologically active substance; and Step (D): a step wherein the protective group of the polyoxyethylene derivative is deprotected.

[2] The method of [1], wherein an acidic solution is used as a solvent in the step (A).

[3] The method of [1] or [2], wherein the step (C) and the step (D) are performed in succession.

[4] The method of any one of [1] to [3], wherein the step (D) is performed under acidic conditions.

[5] The method as claimed in any one of [1] to [3], wherein the step (D) is performed by a reduction reaction.

Effect of the Invention

The invention relates to a novel production method of a high purity polyoxyethylene derivative having a plurality of hydroxyl groups at a terminal, which is suitable for pharmaceutical use. According to the production method, while leaving a hydroxyl group at a 1-position of a polyhydric alcohol, for example, xylitol or volemitol, which is a raw material, an even number of hydroxyl groups can be efficiently protected by benzylidene acetalization. Further, by polymerizing ethylene oxide to the hydroxyl group at the 1-position under specific conditions, it is possible to obtain a high purity polyoxyethylene derivative. Moreover, by functionalizing a hydroxyl group at a terminal of the polyoxyethylene chain obtained and then removing benzylidene acetal, it is possible to obtain a polyoxyethylene derivative having a plurality of hydroxyl groups at a terminal, which can be efficiently modified a physiologically active substance.

MODE FOR CARRYING OUT THE INVENTION

The polyoxyethylene derivative according to the invention is a polyoxyethylene derivative represented by formula (1) (hereinafter, also referred to as "polyoxyethylene derivative (1) of the invention"):

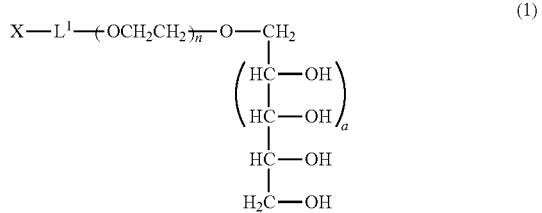

(1)

(in formula (1), $L^1$ is a divalent linker, X is a functional group capable of reacting with a physiologically active substance, a is 1 or 2, and n is from 11 to 3,650.)

The molecular weight of the polyoxyethylene derivative represented by formula (1) is ordinarily from 500 to 160,000, preferably from 1,000 to 80,000, and more preferably from 2,000 to 40,000.

$L^1$ in formula (1) represents a divalent linker which links between the polyoxyethylene and the functional group X capable of reacting with a physiologically active substance by a covalent bond.

The linker is not particularly limited as long as it is a group capable of forming a covalent bond and is preferably one selected from an alkylene group, a phenylene group, an ester bond, an amide bond, an ether bond, a urethane bond, a carbonate bond and a secondary amino group or a combination thereof. The linker is more preferably an alkylene group, a phenylene group or a combination of an ester bond, an amide bond, an ether bond, a urethane bond, a carbonate bond or a secondary amino group with one or two alkylene groups, and those described in group (I) shown below are particularly preferred aspects.

Group (I):

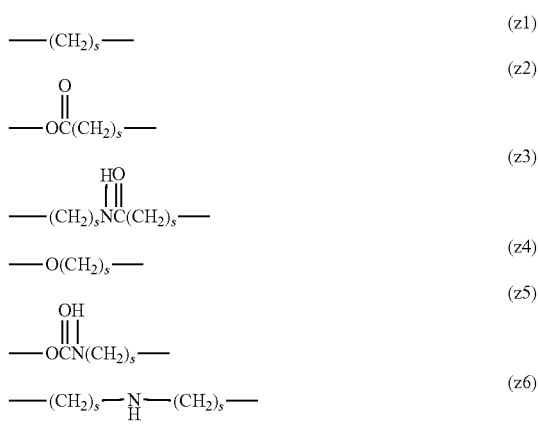

In the formulae (formula (z1) to formula (z6)), s represents 0 or an integer of 1 to 10, preferably an integer of 1 to 6, and more preferably an integer of 1 to 3. Further, in formula (z3) and formula (z6), two s may be the same or different, and are preferably the same.

The functional group capable of reacting with a physiologically active substance represented by X in formula (1) is not particularly limited as long as it is a functional group capable of forming a chemical bond to a functional group, which a physiologically active substance has, for example, an amino group, a mercapto group, an aldehyde group, a carboxyl group, an unsaturated bond or an azide group. Specifically, the functional group includes, for example, an active ester group, an active carbonate group, an aldehyde group, an isocyanate group, an isothiocyanate group, an epoxide group, a carboxyl group, a thiol group, a maleimide group, a substituted maleimide group, a hydrazide group, a dithiopyridine group, a substituted sulfonate group, a vinylsulfone group, an amino group, an oxyamino group, an iodoacetamide group, an alkylcarbonyl group, an alkenyl group, an alkynyl group and an azide group.

In a preferred embodiment, the functional group X can be classified into group (II), group (III), group (IV), group (V), group (VI) and group (VII) described below.

Group (II): Functional group capable of reacting with an amino group, which a physiologically active substance has.

(a), (b-1), (b-2), (c), (d), (e), (f) and (i) described below

Group (III): Functional group capable of reacting with a mercapto group, which a physiologically active substance has.

(a), (b-1), (b-2), (c), (d), (e), (f), (g), (h), (i) and (j) described below

Group (IV): Functional group capable of reacting with an aldehyde group, which a physiologically active substance has.

(g), (k), (l) and (m) described below

Group (V): Functional group capable of reacting with a carboxyl group, which a physiologically active substance has.

(g), (k), (l) and (m) described below

Group (VI): Functional group capable of reacting with an unsaturated bond, which a physiologically active substance has.

(g), (k) and (n) described below

Group (VII): Functional group capable of reacting with an azide group, which a physiologically active substance has.

(j) described below

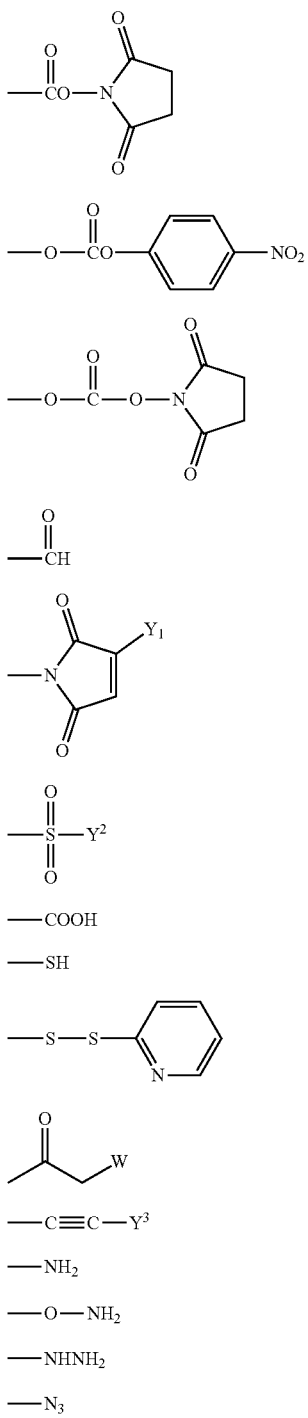

In the functional group (i), W in the formula represents a halogen atom, for example, a chlorine atom (Cl), a bromine atom (Br) or an iodine atom (I), preferably Br or I, and more preferably I.

Further, in the functional group (d) and the functional group (j), $Y^1$ and $Y^3$ in the formulae each independently represents a hydrogen atom or a hydrocarbon group having from 1 to 5 carbon atoms, and preferably a hydrocarbon group having from 1 to 5 carbon atoms. The hydrocarbon group having from 1 to 5 carbon atoms specifically includes, for example, a methyl group, an ethyl group, a propyl group, an isopropyl group, a butyl group and a tertiary butyl group. A methyl group or an ethyl group is preferred.

Further, in the functional group (e), $Y^2$ in the formula represents a hydrocarbon group having from 1 to 10 carbon atoms which may contain a fluorine atom and specifically includes, for example, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group and a 4-(trifluoromethoxy)phenyl group. A methyl group, a vinyl group, a 4-methylphenyl group or a 2,2,2-trifluoroethyl group is preferred.

The active ester group is an ester group in which a carboxyl group is condensed with an alkoxy group having a high leaving ability. The ester group includes, for example, an ester of a carboxyl group with nitrophenol, N-hydroxysuccinimide or pentafluorophenol, and an ester group in which a carboxyl group is condensed with N-hydroxysuccinimide is preferred.

The active carbonate group is a carbonate group having an alkoxy group having a high leaving ability. The alkoxy group having a high leaving ability includes, for example, nitrophenol, N-hydroxysuccinimide and pentafluorophenol, and a carbonate group which is bonded to nitrophenol or N-hydroxysuccinimide is preferred.

The substituted maleimide group is a maleimide group in which a hydrocarbon group is bonded to one carbon atom of the double bond of the maleimide group. The hydrocarbon group specifically includes, for example, a methyl group, an ethyl group, a propyl group, an isopropyl group, a butyl group and a tertiary butyl group. A methyl group or an ethyl group is preferred.

The substituted sulfonate group is a sulfonate group in which a hydrocarbon group which may contain a fluorine atom is bonded to the sulfur atom of the sulfonate group. The hydrocarbon group which may contain a fluorine atom specifically includes, for example, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group and a 4-(trifluoromethoxy)phenyl group. A methyl group, a vinyl group, a 4-methylphenyl group or a 2,2,2-trifluoroethyl group is preferred.

In formula (1), when a is 1, a xylitol structure is represented, and when a is 2, a volemitol structure is represented.

In formula (1), n is an average molar number of oxyethylene groups added, and n1 is ordinarily from 11 to 3,650, preferably from 22 to 1,825, and more preferably from 44 to 910.

The polyoxyethylene derivative of the invention can be produced by performing steps (A), (B), (C) and (D) as described below.

The step (A) is a step wherein while leaving only a hydroxyl group at a 1-position of a polyhydric alcohol having 5 or 7 hydroxyl groups, the remaining 4 or 6 hydroxyl groups are protected by cyclic benzylidene acetalization to obtain a compound having the hydroxyl group at the 1-position and a protective group of a cyclic benzylidene acetal structure.

The step (B) is a step wherein from 11 to 3,650 moles of ethylene oxide are polymerized to the compound obtained in the step (A) to obtain a polyoxyethylene derivative.

The step (C) is a step wherein the hydroxyl group at a terminal of the polyoxyethylene derivative obtained in the step (B) is converted to the functional group capable of reacting with a physiologically active substance described above. Depending on the kind of the functional group, the functionalization may be further performed after deacetalization of the step (D). Also, depending on the kind of the functional group, during the functionalization the deacetalization of the step (D) may be performed at the same time.

The step (D) is a step wherein the protective group of the polyoxyethylene derivative described above is deprotected to produce hydroxyl groups by cleaving the acetal ring of the cyclic acetal structure.

By performing the steps (A), (B), (C) and (D) described above, the polyoxyethylene derivative (1) represented by formula (1) can be produced.

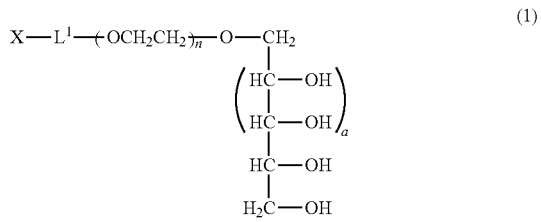

(in formula (1), $L^1$, X, a and n are same as defined above.)

Preferred specific examples of the production method of the polyoxyethylene derivative (1) will be further described below. Since the derivative can be produced by the same method in both cases of a=1 and a=2, the description is made as to a derivative wherein a=1, that is, a polyoxyethylene derivative (2) represented by formula (2) described below (polyoxyethylene derivative (2)). The production conditions described below are similarly applied to a polyoxyethylene derivative wherein a=2.

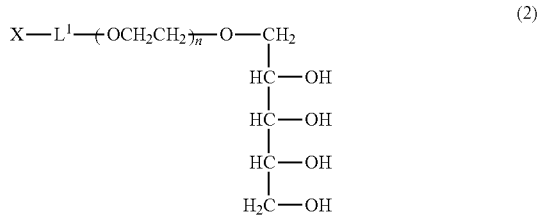

(in the formula, $L^1$, X and n have the same meanings as defined above.)

The polyoxyethylene derivative (2) can be produced by performing steps (A), (B), (C) and (D) described below in this order.

The step (A) is a step wherein while leaving only a hydroxyl group at a 1-position of xylitol having 5 hydroxyl groups, 4 hydroxyl groups are protected by cyclic benzylidene acetalization. In this step, a high purity 2,3,4,5-dibenzylidene xylitol can be obtained. 1,2,4,5-dibenzylidene xylitol which is a structural isomer leaving a hydroxyl group at a 3-position is not formed in the step (A). It can be confirmed by $^1$H-NMR analysis that the structural isomer is not contained.

The method for acetalization is not particularly limited as long as it is a common protection method of a hydroxyl group as described, for example, in Protective Groups in Organic Synthesis (Theodora W. Greene, et al.). Specifically, by reacting benzaldehyde to xylitol in the presence of an acid catalyst, for example, sulfuric acid, hydrochloric acid, phosphoric acid, p-toluenesulfonic acid or p-toluenesulfonic acid monohydrate, 2,3,4,5-dibenzylidene xylitol can be obtained.

The amount of the acid used is preferably from $5 \times 10^{-6}$ to $5 \times 10^{-3}$ equivalents and more preferably from $5 \times 10^{-5}$ to $5 \times 10^{-4}$ equivalents with respect to xylitol.

Further, in order to dissolve xylitol, a large amount of acid may be used as a solvent. In such a case, the amount of the acid used is preferably from 5 to 100 times by weight and more preferably from 10 to 50 times by weight with respect to xylitol. As to the kind of the acid, sulfuric acid, hydrochloric acid or phosphoric acid is suitable, sulfuric acid or hydrochloric acid is preferred, and sulfuric acid is more preferred.

The amount of benzaldehyde used is preferably from 2.0 to 5.0 equivalents and more preferably from 2.5 to 4.0 equivalents with respect to xylitol.

In the reaction, a solvent, for example, dimethylformamide, tetrahydrofuran or dichloromethane cab be used, and dimethylformamide or tetrahydrofuran is preferred.

The reaction temperature is ordinarily from 0 to 60° C. and preferably from 10 to 50° C. The reaction time is preferably from 3 to 24 hours. When the reaction time is short, the reaction becomes insufficient.

Unacetalized xylitol, impurities and the like in the reaction are preferably removed. The 2,3,4,5-dibenzylidene xylitol formed by the reaction is crystallized in the reaction solution so that purification can be performed only by filtration. Since the crystals obtained have low solubility in any solvent, as to a method for further increasing the purity, the impurities can be removed by repeating suspension of the crystals in a solvent, stirring and filtration. As the solvent used for the suspension washing, a solvent, for example, water, methanol, ethanol, diethyl ether, methyl tert-butyl ether, THF or acetonitrile is preferred, and a mixed solution thereof may be used. The washing temperature is ordinarily from 0 to 60° C. and preferably from 10 to 50° C. The stirring time is preferably from 10 minutes to 3 hours. When the stirring time is short, the purification becomes insufficient.

The step (B) is composed of two steps of (B1) and (B2) described below.

The step (B1) is a step of alcoholation of 2,3,4,5-dibenzylidene xylitol, and sodium methoxide, potassium tert-butoxide, potassium methoxide or the like is used as a catalyst.

The step (B2) is a step of addition polymerization of ethylene oxide at a reaction temperature from 50 to 130° C.

In the step (B-1), as a catalyst, sodium methoxide, potassium tert-butoxide, potassium methoxide or potassium hydroxide, preferably sodium methoxide is added in an amount from 5 to 50% by mole and the reaction is performed at 20 to 80° C. The solvent used in the alcoholation reaction is not particularly limited as long as it is an aprotic solvent, for example, toluene, benzene, xylene, acetonitrile, tetrahydrofuran, dimethyl sulfoxide, dimethylformamide or dimethylacetamide and preferably toluene. The amount of the solvent used is from 1 to 50 times by weight and preferably from 2 to 30 times by weight with respect to 2,3,4,5-dibenzylidene xylitol. Further, since 2,3,4,5-dibenzylidene xylitol is easy to absorb moisture and contains moisture, it is preferred to perform dehydration operation by azeotropy and it is more preferred to perform it twice before the addition of ethylene oxide.

When the catalyst amount is less than 5% by mole, since the polymerization reaction rate of ethylene oxide decreases and impurities, for example, terminal vinyl ether compound are produced due to a long time high temperature reaction, the catalyst amount of 5% by mole or more is advantageous in view of the production of a high quality high-molecular weight compound. When the catalyst amount exceeds 50% by mole, the viscosity of the reaction solution increases or the solution solidifies at the alcoholation reaction and thus there is a tendency that the stirring efficiency decreases and the alcoholation is not accelerated. Further, when the solution solidifies, handling thereof tends to be difficult, thereby causing moisture absorption. When the alcoholate has absorbed water, a polyalkylene glycol compound derived from water is formed and is contained as an impurity undesirable for pharmaceutical uses.

As to the reaction temperature, when the temperature is lower than 20° C., the reaction rate of the exchange reaction decreases and an alcohol, for example, methanol remains to cause addition polymerization with ethylene oxide, whereby an impurity having a molecular weight same as the molecular weight of the desired compound is formed. When the temperature is higher than 80° C., a decomposition reaction occurs. Since the decomposition reaction tends to occur in the alcoholation reaction, it is desired to set the reaction time from 1 to 3 hours.

The step (B2) is a step of addition polymerization of ethylene oxide at a reaction temperature from 50 to 130° C. to obtain the desired compound in which polyoxyethylene is introduced into the 1-position of 2,3,4,5-dibenzylidene xylitol. When the reaction temperature is lower than 50° C., the polymerization reaction rate is low and there is a tendency to decrease the quality of the desired compound. Further, when the temperature is higher than 130° C., a side reaction, for example, vinyl etherification of the terminal occurs during the polymerization and there is a tendency to decrease the quality of the desired compound. During the polymerization, as the molecular weight increases, the viscosity of the reaction solution increases, so that an aprotic solvent, preferably toluene may be appropriately added. The reaction pressure is preferably controlled from 0.03 to 1.0 MPa.

The 2,3,4,5-dibenzylidene xylitol is poor in solubility and is dispersed in a solvent so that it is impossible to add ethylene oxide under reaction conditions, for example, normal pressure. However, by using a suitable catalyst under high temperature and high pressure reaction conditions, it is possible to add ethylene oxide to the hydroxyl group at the 1-position.

The step (C) is a step of functionalizing the hydroxyl group at the terminal of the polyoxyethylene derivative obtained in the step (B). Depending on the kind of the functional group, during the functionalization the deacetalization of the step (D) may be performed at the same time.

The hydroxyl group at the terminal of the polyoxyethylene derivative obtained in the step (B) can be modified to each of various functional groups shown in group (II), group (III), group (IV), group (V), group (VI) and group (VII).

Further, using a compound having each of the functional groups in group (II), group (III), group (IV), group (V), group (VI) and group (VII) as an intermediate, functionalization can be performed by further reacting the compound with the other compound. For example, using an intermediate having a functional group of (k) as a raw material, the functional groups of (a) and (d) can be obtained.

The method for introducing a functional group into the hydroxyl group at the terminal of the polyoxyethylene derivative will be described in detail below.

[Method for Introducing Functional Groups (b) and (e)]

By reacting the hydroxyl group at the terminal of the polyoxyethylene derivative with an organic base, for example, triethylamine, pyridine or 4-dimethylaminopyridine or an inorganic base, for example, sodium carbonate, sodium hydroxide, sodium hydrogen carbonate, sodium acetate, potassium carbonate or potassium hydroxide and any one of the compounds represented by formulae (b1) and (e1) (compound (b1) and compound (e1)) shown below in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or without any solvent, the functional groups (b) and (e) can be introduced, respectively (compound (b) or (e) into which the functional group (b) or (e) has been introduced is obtained).

The ratio of the organic base or inorganic base used is not particularly limited and is preferably equimolar or more with respect to the polyoxyethylene derivative. Further, the organic base may be used as a solvent. $W^2$ in formula (b1) or formula (e1) is a halogen atom selected from Cl, Br and I, and is preferably Cl. The ratio of the compounds (b1) and (e1) used is not particularly limited and is preferably equimolar or more and more preferably, the compounds are reacted in the range from equimolar to 50 times by mole with respect to the polyoxyethylene derivative. The reaction temperature is preferably from 0 to 300° C. and more preferably from 20 to 150° C. The reaction time is preferably from 10 minutes to 48 hours and more preferably from 30 minutes to 24 hours. The compound formed may be purified by a purification means, for example, extraction, recrystallization, adsorption treatment, reprecipitation, column chromatography or supercritical extraction.

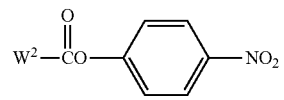
(b1)

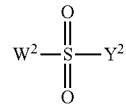
(e1)

(in the formulae, $W^2$ represents a halogen atom selected from Cl, Br and I, and $Y^2$ represents a hydrocarbon group having from 1 to 10 carbon atoms which may contain a fluorine atom.)

[Method for Introducing Functional Group (f)]

A carboxyl body (f) into which the functional group (f) has been introduced can be obtained by reacting the hydroxyl group at the terminal of the polyoxyethylene derivative or an amine (k) described later with a dicarboxylic acid anhydride, for example, succinic anhydride or glutaric anhydride. The reaction of the compound (8) or the amine (k) with the dicarboxylic acid anhydride is performed in the aprotic solvent described above or without any solvent.

The ratio of the dicarboxylic acid anhydride used is not particularly limited and is preferably equimolar or more and more preferably from equimolar to 5 times by mole with respect to the polyoxyethylene derivative. The reaction temperature is preferably from 0 to 200° C. and more preferably from 20 to 150° C. The reaction time is preferably from 10 minutes to 48 hours and more preferably from 30 minutes to 12 hours. In the reaction, an organic base, for example, triethylamine, pyridine or dimethylaminopyridine or an inorganic base, for example, sodium carbonate, sodium hydroxide, sodium hydrogen carbonate, sodium acetate, potassium carbonate or potassium hydroxide may be used as a catalyst. The ratio of the catalyst used is preferably from 0.1 to 50% by weight and more preferably from 0.5 to 20% by weight. The carboxyl body (f) thus formed may be purified by a purification means, for example, extraction, recrystallization, adsorption treatment, reprecipitation, column chromatography or supercritical extraction, or in the case where it is used as a raw material for a condensation reaction, it may be used as it is.

The carboxyl body (f) can be obtained by reacting the hydroxyl group at the terminal of the polyoxyethylene derivative with a halogenated alkyl ester, for example, ethyl 6-bromohexanoate or ethyl 7-bromoheptanoate. The etherification reaction of the hydroxyl group at the terminal of the polyoxyethylene derivative with a halogenated alkyl ester is performed in the aprotic solvent described above or without any solvent.

The ratio of the halogenated alkyl ester used is not particularly limited and is preferably equimolar or more and more preferably from equimolar to 30 times by mole with respect to the polyoxyethylene derivative. The reaction temperature is preferably from 0 to 200° C. and more preferably from 20 to 150° C. The reaction time is preferably from 10 minutes to 48 hours and more preferably from 30 minutes to 12 hours. In the reaction, an organic base, for example, triethylamine, pyridine or dimethylaminopyridine or an inorganic base, for example, sodium carbonate, sodium hydroxide, sodium hydrogen carbonate, sodium acetate, potassium carbonate or potassium hydroxide may be used as a catalyst. The ratio of the catalyst used is preferably from 0.1 to 500% by weight and more preferably from 0.5 to 300% by weight.

After the etherification, hydrolysis of the ester is performed by adding an aqueous solution of sodium hydroxide, potassium hydroxide or the like in the case of the organic base or water in the case of the inorganic base. The reaction temperature is preferably from 0 to 100° C. and more preferably from 20 to 100° C. The reaction time is preferably from 10 minutes to 48 hours and more preferably from 30 minutes to 12 hours. After the reaction, neutralization is performed with hydrochloric acid, sulfuric acid or the like. The carboxyl body (f) thus formed may be purified by a purification means, for example, extraction, recrystallization, adsorption treatment, reprecipitation, column chromatography or supercritical extraction, or in the case where it is used as a raw material for a condensation reaction, it may be used as it is.

[Method for Introducing Functional Group (a)]

A succinimide body (a) into which the functional group (a) has been introduced can be obtained by subjecting the carboxyl body (f) to a condensation reaction with N-hydroxysuccinimide in the presence of a condensing agent, for example, dicyclohexylcarbodiimide (DCC) or 1-ethyl-3-(3-dimethylaminopropyl)carbodiimide hydrochloride (EDC). The condensation reaction is performed in the aprotic solvent described above or without any solvent. The condensing agent is not particularly limited and is preferably DCC. The ratio of DCC used is preferably equimolar or more and more preferably from equimolar to 5 times by mole with respect to the carboxyl body (f). The ratio of N-hydroxysuccinimide used is preferably equimolar or more and more preferably from equimolar to 5 times by mole with respect to the carboxyl body (f). The reaction temperature is preferably from 0 to 100° C. more preferably from 20 to 80° C. The reaction time is preferably from 10 minutes to 48 hours and more preferably from 30 minutes to 12 hours. The succinimide body (a) formed may be purified by a purification means, for example, extraction, recrystallization, adsorption treatment, reprecipitation, column chromatography or supercritical extraction.

Further, the succinimide body (a) can be obtained by reacting the hydroxyl group at the terminal of the polyoxyethylene derivative with N,N'-disuccinimide carbonate. The reaction is performed in the aprotic solvent described above or without any solvent same as in the reaction described above. The ratio of N,N'-disuccinimide carbonate used is preferably equimolar or more and more preferably from equimolar to 5 times by moles with respect to the polyoxyethylene derivative. The reaction temperature is preferably from 0 to 100° C. and preferably from 20 to 80° C. The reaction time is preferably from 10 minutes to 48 hours and more preferably from 30 minutes to 12 hours. The compound formed may be purified by a purification means, for example, extraction, recrystallization, adsorption treatment, reprecipitation, column chromatography or supercritical extraction.

[Method for Introducing Functional Group (k)]

A nitrile body can be obtained by adding acrylonitrile or the like to the hydroxyl group at the terminal of the polyoxyethylene derivative in a solvent, for example, water or acetonitrile using an inorganic base, for example, sodium hydroxide or potassium hydroxide as a catalyst. Then, a hydrogenation reaction of the nitrile group is performed under a nickel or palladium catalyst in an autoclave to obtain an amine body (k) having the functional group (k). The ratio of the inorganic base used when the nitrile body is obtained is not particularly limited and is preferably from 0.01 to 50% by weight with respect to the polyoxyethylene derivative. The ratio of acrylonitrile or the like used is not particularly limited and is preferably from 0.5 to 5 times by weight with respect to the weight of the polyoxyethylene derivative and it is more preferred to perform the reaction in the range from 1 to 4 times by weight. Further, acrylonitrile may be used as a solvent. The reaction temperature is preferably from −50 to 100° C. and more preferably from −20 to 60° C. The reaction time is preferably from 10 minutes to 48 hours and more preferably from 30 minutes to 24 hours.

A reaction solvent in the subsequent hydrogenation reaction of the nitrile body is not particularly limited as long as it is a solvent which is not involved in the reaction and is preferably toluene. The ratio of the nickel or palladium catalyst used is not particularly limited and is from 0.05 to 30% by weight and preferably from 0.5 to 20% by weight with respect to the nitrile body. The reaction temperature is preferably from 20 to 200° C. and more preferably from 50 to 150° C. The reaction time is preferably from 10 minutes to 48 hours and more preferably from 30 minutes to 24 hours. A hydrogen pressure is preferably from 2 to 10 MPa and more preferably from 3 to 8 MPa. Further, in order to prevent dimerization, ammonia may be added to the reaction system. An ammonia pressure in the case of adding ammonia is not particularly limited and is from 0.1 to 10 MPa and more preferably from 0.3 to 2 MPa. The compound formed may be purified by the purification means described above.

The amine body (k) can also be obtained by reacting the compound (e) with aqueous ammonia. The reaction is performed in aqueous ammonia, and the concentration of ammonia is not particularly limited and is preferably in the range from 10 to 40%. The ratio of the aqueous ammonia used is preferably from 1 to 300 times the weight of the compound (e). The reaction temperature is preferably from 0 to 100° C. and more preferably from 20 to 80° C. The reaction time is preferably from 10 minutes to 72 hours and more preferably from 1 to 36 hours. Further, the amine body (k) can be also obtained by reacting the compound (e) with ammonia in an autoclave. A reaction solvent is not particularly limited and preferably includes methanol and ethanol. The amount of ammonia is preferably from 10 to 300% by weight and more preferably from 20 to 200% by weight with respect to the compound (e). The reaction temperature is preferably from 50 to 200° C. and more preferably from 80 to 150° C. The reaction time is preferably from 10 minutes to 24 hours and more preferably from 30 minutes to 12 hours. The compound formed may be purified by the purification means described above.

Further, the amine body (k) can be obtained by bonding the hydroxyl group at the terminal of the polyoxyethylene derivative to phthalimide in an aprotic solvent by Mitsunobu reaction, followed by deprotection with a polyvalent amine. The reaction conditions of the Mitsunobu reaction are not particularly limited and chloroform or dichloromethane is preferred as the reaction solvent. Further, it is preferred to use triphenylphosphine in an amount of equimolar or more and preferably from equimolar to 50 times by mole with respect to the polyoxyethylene derivative and diisopropyl azodicarboxylate in an amount of equimolar or more and preferably from equimolar to 50 times by mole with respect to the polyoxyethylene derivative. The reaction temperature is preferably from 0 to 100° C. and more preferably from 10 to 50° C. The reaction time is preferably from 10 minutes to 72 hours and more preferably from 30 minutes to 6 hours.

As to the deprotection, a polyvalent amine, for example, hydrazine or ethylenediamine is used in an amount of equimolar or more and preferably from equimolar to 500 times by mole with respect to the polyoxyethylene derivative. A reaction solvent is not particularly limited and methanol is preferred. The reaction temperature is preferably from 0 to 100° C. and more preferably from 20 to 80° C. The reaction time is preferably from 10 minutes to 72 hours and more preferably from 1 to 10 hours. The compound formed may be purified by a purification means, for example, extraction, recrystallization, adsorption treatment, reprecipitation, column chromatography or supercritical extraction.

[Method for Introducing Functional Group (d)]

A maleimide body (d) into which the functional group (d) has been introduced can be obtained by reacting the amino group of the amine body (k) obtained by the method described above with maleic anhydride in the aprotic solvent described above or without any solvent to obtain a maleimide body and then subjecting it to a ring closure reaction using acetic anhydride and sodium acetate as catalysts. The ratio of maleic anhydride used in the maleimidation reaction is not particularly limited and is preferably equimolar or more and more preferably from equimolar to 5 times by mole with respect to the amine body (k). The reaction temperature is preferably from 0 to 200° C. and more preferably from 20 to 120° C. The reaction time is preferably from 10 minutes to 48 hours and more preferably from 30 minutes to 12 hours. The maleimide body (d) formed may be purified by the purification means described above or may be used as it is in the subsequent ring closure reaction.

A reaction solvent in the subsequent ring closure reaction is not particularly limited and is preferably an aprotic solvent or acetic anhydride. The ratio of sodium acetate used is not particularly limited and is preferably equimolar or more and more preferably from equimolar to 50 times by mole with respect to the maleimide body (d). The reaction temperature is preferably from 0 to 200° C. and more preferably from 20 to 150° C. The reaction time is preferably from 10 minutes to 48 hours and more preferably from 30 minutes to 12 hours. The compound formed may be purified by the purification means described above.

The maleimide body (d) described above can also be obtained by reacting the compound (d1) represented by formula (d1) shown below with the amino group of the amine body (k) described above. The reaction is performed in the aprotic solvent described above or without any solvent, and the compound (d1) is added in an amount of equimolar or more with respect to the amino group of the amine body (k) to be reacted. The ratio of the compound (d1) used is preferably equimolar or more and more preferably from equimolar to 5 times by mole with respect to the amino group of the amine body (k). The reaction temperature is preferably from 0 to 200° C. and more preferably from 20 to 80° C. The reaction time is preferably from 10 minutes to 48 hours and more preferably from 30 minutes to 12 hours. During the reaction, light shielding may be conducted. The compound formed may be purified by the purification means described above.

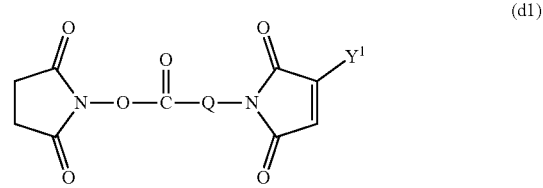

(in the formula, Q represents a hydrocarbon group having from 1 to 9 carbon atoms and $Y^1$ represents a hydrogen atom or a hydrocarbon having from 1 to 5 carbon atoms.)

[Method for Introducing Functional Group (i)]

The functional group (i) can be obtained by reacting the amine of the amine body (k) obtained by the method described above with iodoacetic anhydride in the aprotic solvent described above or without any solvent. The ratio of iodoacetic anhydride used is not particularly limited and is preferably equimolar or more and more preferably from equimolar to 5 times by mole with respect to the amino group of the amine body (k). The reaction temperature is preferably from 0 to 200° C. and more preferably from 20 to 120° C. The reaction time is preferably from 10 minutes to 48 hours and more preferably from 30 minutes to 12 hours. The compound (i) formed having the functional group (i) may be purified by a purification means, for example, extraction, recrystallization, adsorption treatment, reprecipitation, column chromatography or supercritical extraction.

Further, the functional group (i) can be obtained by subjecting the amine body (k) to a condensation reaction with iodoacetic acid in the presence of a condensing agent, for example, DCC or EDC. The condensation reaction is also performed similarly in the aprotic solvent described above or without any solvent. The condensing agent is not particularly limited and is preferably DCC. The ratio of DCC used is preferably equimolar or more and more preferably from equimolar to 5 times by mole with respect to the amine body (k). The ratio of iodoacetic acid used is preferably equimolar or more and more preferably from equimolar to 5 times by mole with respect to the amine body (k). The reaction temperature is preferably from 0 to 100° C. and more preferably from 20 to 80° C. The reaction time is preferably from 10 minutes to 48 hours and more preferably from 30 minutes to 12 hours. The compound formed may be purified by the purification means described above.

[Method for Introducing Functional Group (l)]

An oxyphthalimide body into which the oxyphthalimido group has been introduced can be obtained by reacting the carbonate body (b) with the compound represented by formula (11) shown below (compound (11)) in the presence of an alkali catalyst, for example, triethylamine or pyridine. The reaction can be performed without solvent or under a polar solvent. The solvent is not particularly limited and is preferably methanol. The ratio of the alkali catalyst used is not particularly limited and is preferably equimolar or more and more preferably from equimolar to 20 times by mole with respect to the carbonate body (b). The ratio of the compound (11) used is preferably equimolar or more and more preferably from equimolar to 20 times by mole with respect to the carbonate body (b). The reaction temperature is preferably from 0 to 100° C. and more preferably from 20 to 80° C. The reaction time is preferably from 10 minutes to 48 hours and more preferably from 30 minutes to 12 hours. The compound formed may be purified by a purification means, for example, extraction, recrystallization, adsorption treatment, reprecipitation, column chromatography or supercritical extraction or may be used in the subsequent step without purification.

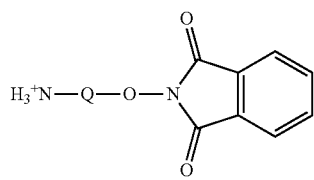

(11)

(in the formula, Q represents a hydrocarbon group having from 1 to 9 carbon atoms.)

The oxyphthalimide body can be also obtained by bonding the hydroxyl group at the terminal of the polyoxyethylene derivative to hydroxyphthalimide in an aprotic solvent by Mitsunobu reaction, followed by deprotection with a polyvalent amine. The reaction conditions for the Mitsunobu reaction are not particularly limited and chloroform or dichloromethane is preferred as the reaction solvent. Further, it is preferred to use triphenylphosphine in an amount of equimolar or more and preferably from equimolar to 50 times by mole with respect to the polyoxyethylene derivative and diisopropyl azodicarboxylate in an amount of equimolar or more and preferably from equimolar to 50 times by mole with respect to the polyoxyethylene derivative. The reaction temperature is preferably from 0 to 100° C. and more preferably from 10 to 50° C. The reaction time is preferably from 10 minutes to 72 hours and more preferably from 30 minutes to 6 hours.

An oxyamine body (1) into which the functional group (1) has been introduced can be obtained by reacting the oxyphthalimide body obtained by any of these methods in the presence of a polyvalent amine, for example, hydrazine or ethylenediamine.

A reaction solvent is not particularly limited and is preferably methanol, dichloromethane or water. The ratio of the polyvalent amine used is not particularly limited and is preferably equimolar or more and more preferably from equimolar to 50 times by mole with respect to the oxyphthalimide body. The reaction temperature is preferably from 0 to 100° C. and more preferably from 20 to 80° C. The reaction time is preferably from 10 minutes to 48 hours and more preferably from 30 minutes to 12 hours. The compound formed may be purified by a purification means, for example, extraction, recrystallization, adsorption treatment, reprecipitation, column chromatography or supercritical extraction.

[Method for Introducing Functional Group (c)]

An aldehyde body (c) having the functional group (c) can be obtained by reacting the compound (e) with an acetal compound represented by formula (c1) shown below (compound (c1)) to obtain an acetal body and then subjecting it to hydrolysis under an acidic condition. The acetalization reaction can be performed by reacting the compound (e) with an equimolar or more amount and preferably from equimolar to 50 times by mole of the compound (c1) in the aprotic solvent described above or without any solvent. The compound (c1) can be prepared from the corresponding alcohol using metal sodium, metal potassium, sodium hydride, potassium hydride, sodium methoxide, potassium tert-butoxide or the like. The reaction temperature is preferably from 0 to 300° C. and more preferably from 20 to 150° C. The reaction time is preferably from 10 minutes to 48 hours and more preferably from 30 minutes to 24 hours.

In the case of using the compound represented by formula (c2) shown below (compound (c2)), an acetal body can be obtained by converting the hydroxyl group at the terminal of the polyoxyethylene derivative into an alcoholate by the method described above and then reacting it with the compound (c2) in a ratio of equimolar or more and preferably from equimolar to 100 times by mole in the aprotic solvent described above or without any solvent. The reaction temperature is preferably from 0 to 300° C. and more preferably from 20 to 150° C. The reaction time is preferably from 10 minutes to 48 hours and more preferably from 30 minutes to 24 hours.

In the case of using the compound represented by formula (c3) shown below (compound (c3)), an acetal body can be obtained by reacting the compound into which the functional group (a), (b), (e) or (f) described above has been introduced (compound (a), (b), (e) or (f)) with the compound (c3). A solvent for the reaction is not particularly limited and the reaction is preferably performed in the aprotic solvent described above. The charging ratio of the compound (c3) is preferably equimolar or more and more preferably from equimolar to 10 times by mole with respect to the compound (a), (b), (e) or (f). The reaction temperature is preferably from −30 to 200° C. and more preferably from 0 to 150° C. The reaction time is preferably from 10 minutes to 48 hours and more preferably from 30 minutes to 24 hours. In the case of using the compound (f), a condensing agent, for example, DCC or EDC may be used. Any acetalization reaction may be conducted under light shielding. The acetal body thus obtained may be purified by the purification means described above or may be used as it is without purification in the subsequent aldehydation reaction.

The aldehyde body (c) can be obtained by hydrolyzing the acetal body in a 0.1 to 50% aqueous solution which is adjusted to pH 1 to 4 with an acid, for example, acetic acid, phosphoric acid, sulfuric acid or hydrochloric acid. The reaction temperature is preferably from −20 to 100° C. and more preferably from 0 to 80° C. The reaction time is preferably from 10 minutes to 24 hours and more preferably from 30 minutes to 10 hours. The reaction may be conducted under light shielding. The compound formed may be purified by the purification means described above. Further, in the aldehydation, it is possible to simultaneously perform deacetalization of the step (D).

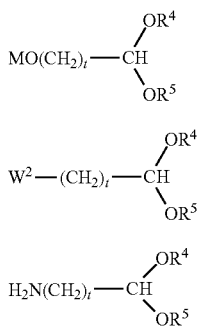

(in each of the formulae described above, $R^4$ and $R^5$ each independently represent a hydrocarbon group having from 1 to 3 carbon atoms and may be the same or different from each other, or they may bond to each other to form a ring. M represents sodium or potassium, $W^2$ is a halogen atom selected from Cl, Br and I, and t is an integer of 1 to 5.)

[Method for Introducing Functional Group (g)]

A mercapto body having the functional group (g) (compound (g)) can be obtained by reacting the compound (e) with a thiation agent, for example, thiourea. The compound (e) is produced in the manner as described above. The thiation reaction is performed in a solvent, for example, water, an alcohol or acetonitrile or without any solvent. The ratio of thiourea used is preferably equimolar or more and more preferably in the range from equimolar to 50 times by mole with respect to the compound (e). The reaction temperature is preferably from 0 to 300° C. and more preferably from 20 to 150° C. The reaction time is preferably from 10 minutes to 48 hours and more preferably from 30 minutes to 24 hours. After the reaction, the mercapto body can be obtained by subjecting the thiazolium salt formed to alkaline hydrolysis. The compound formed may be purified by the purification means described above. Further, in the mercaptation, it is possible to simultaneously perform deacetalization of the step (D) during the pH adjustment after the hydrolysis.

Further, the mercapto body described above can also be obtained by reacting the compound (e) with a compound represented by formula (g1) shown below (compound (g1)), followed by decomposition with a primary amine. The reaction of the compound (e) with the compound (g1) is performed in the aprotic solvent described above or without any solvent. The ratio of the compound (g1) used is preferably equimolar or more and more preferably from equimolar to 50 times by mole with respect to the compound (e). The reaction temperature is preferably from 0 to 300° C. and more preferably from 20 to 80° C. The reaction time is preferably from 10 minutes to 48 hours and more preferably from 30 minutes to 24 hours. The subsequent alkali decomposition with a primary amine is performed in the aprotic solvent described above or without any solvent. The primary amine used is not particularly limited and preferably includes, for example, ammonia, methylamine, ethylamine, propylamine, butylamine, pentylamine, hexylamine, cyclohexylamine, ethanolamine, propanolamine and butanolamine. Naturally, the primary amine may be used as a solvent. The compound formed may be purified by the purification means described above.

[Method for Introducing Functional Group (h)]

A compound having the functional group (h) (compound (h)) can be obtained by reacting the compound (g) with 2,2-dipyridyl disulfide. In the reaction, a solvent is not particularly limited and the reaction is preferably performed in an alcohol. The ratio of 2,2-dipyridyl disulfide charged is preferably equimolar or more and more preferably from equimolar to 50 times by mole with respect to the compound (g). The reaction temperature is preferably from −30 to 100° C. and more preferably from 0 to 60° C. The reaction time is preferably from 10 minutes to 48 hours and more preferably from 30 minutes to 24 hours. The acetal body thus-obtained may be purified by the purification means described above.

[Method for Introducing Functional Group (m)]

The compound having the functional group (m) (compound (m)) can be obtained by reacting the compound (a), (b), (c) or (e) described above with tert-butyl carbazate in the aprotic solvent described above or without any solvent and deprotecting the tert-butoxycarbonyl group (Boc group). The ratio of tert-butyl carbazate used is not particularly limited and is preferably equimolar or more and more preferably from equimolar to 10 times by mole with respect to the compound (a), (b), (c) or (e). The reaction temperature is preferably from 0 to 200° C. and more preferably from 20 to 80° C. The reaction time is preferably from 10 minutes to 48 hours and more preferably from 30 minutes to 12 hours. The compound (m) formed may be purified by the purification means described above. Further, it is possible to simultaneously perform deacetalization of the step (D) during the deprotection of the Boc group.

[Method for Introducing Functional Group (j)]

An acetylene compound having the functional group (j) (compound (j)) can be obtained by reacting the compound (a), (b), (c) or (e) described above with an acetylene compound represented by formula (j 1) shown below (compound (j 1)). The acetylation reaction can be performed by reacting the compound (j 1) in an amount of equimolar or more and preferably from equimolar to 50 times by mole with respect to the compound (a), (b), (c) or (e) in a protic solvent or without any solvent. The reaction temperature is preferably from 0 to 300° C. and more preferably from 20 to 150° C. The reaction time is preferably from 10 minutes to 48 hours and more preferably from 30 minutes to 24 hours. The compound formed may be purified by the purification means described above.

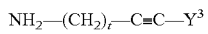 (j1)

(in the formula, t is an integer of 1 to 5, and $Y^3$ represents a hydrogen atom or a hydrocarbon group having from 1 to 5 carbon atoms.)

[Method for Introducing Functional Group (n)]

An azide compound having the functional group (n) (compound (n)) can be obtained by reacting the amine body (k) obtained by the method as described above with the compound represented by formula (n1) shown below (compound (n1)) in the presence of a condensing agent, for example, DCC or EDC. The condensation reaction is performed in the aprotic solvent described above or without any solvent. The condensing agent is not particularly limited and is preferably DCC. The ratio of DCC used is preferably equimolar or more and more preferably from equimolar to 5 times by mole with respect to the amine body (k). The ratio of the compound (n1) used is preferably equimolar or more and more preferably from equimolar to 5 times by mole with respect to the compound (k). The reaction temperature is preferably from 0 to 100° C. and more preferably from 20 to 80° C. The reaction time is preferably from 10 minutes to 48 hours and more preferably from 30 minutes to 12 hours. The compound formed may be purified by the purification means described above.

(n1)

(in the formula, Q represents a hydrocarbon group having from 1 to 9 carbon atoms.)

The step (D) is a deprotection step of cleaving the cyclic benzylidene acetal structure of the polyoxyethylene derivative into which the functional group is introduced in the step (C). Depending on the kind of the functional group, functionalization can be further performed after the deacetalization in the step (D).

A method of deprotection of the cyclic acetal structure is not particularly limited as long as it is a common deprotection method as described, for example, in Protective Groups in Organic Synthesis (Theodora W. Greene, et al.). Specifically, the deprotection can be performed in the presence of an acid catalyst. The acid catalyst includes, for example, acetic acid, hydrochloric acid, phosphoric acid, p-toluenesulfonic acid and trifluoroacetic acid, and is preferably hydrochloric acid, phosphoric acid or trifluoroacetic acid and more preferably phosphoric acid.

The amount of the acid used is preferably from 0.05 to 2 times by weight and more preferably from 0.1 to 1 time by weight with respect to the compound (9). A solvent used for the deprotection reaction includes water, methanol, ethanol, acetonitrile, tetrahydrofuran, dioxane, dimethyl sulfoxide, dimethylformamide and dimethylacetamide, and is preferably water or methanol. The amount of the solvent used is from 1 to 50 times by weight, preferably from 2 to 35 times by weight and more preferably from 5 to 20 times by weight with respect to the compound (8).

The reaction time is preferably from 1 to 24 hours. When the reaction time is shorter than 1 hour, the deprotection reaction proceeds insufficiently. When the reaction time is longer than 24 hours, there is a concern that oxidative decomposition of polyoxyethylene by an acid and deactivation of the functional group may occur. The reaction temperature is usually from 0 to 60° C. and preferably from 10 to 40° C.

After the deprotection, the product may be purified by a purification means, for example, extraction, recrystallization, adsorption treatment, reprecipitation or supercritical extraction. Preferably, the product is subjected to recrystallization and the resulting crystals are dried under a reduced pressure to obtain the compound (9).

After the deacetalization in the step (D), functionalization can be further performed. It is desired to perform the functionalization after the step (D) for the functional group which may be reacted or decomposed under the deacetalization conditions.

According to the invention, the polyoxyethylene derivative (1) having a plurality of hydroxyl groups at a terminal can be industrially produced in high purity and in an efficient manner.

Further, the polyoxyethylene derivative (1) obtained according to the invention has an advantage that half-life in blood and antigenicity can be improved in comparison with conventional polyoxyethylene derivatives and thus it is useful for modifying physiologically active substances.

EXAMPLE

The invention will be described more specifically based on the examples below. In the examples, $^1$H-NMR and GPC were used for analysis and identification of the compounds.
<Analysis Method of $^1$H-NMR>

In $^1$H-NMR analysis, JNM-ECP400 manufactured by JEOL Datum Ltd. was used. The integral values in NMR measurement value are theoretical values.
<Analysis Method of GPC Analysis>

The GPC analysis was performed under the conditions described below.

Apparatus: Shimadzu LC-10Avp
Column: PL gel MIXED-D×2 (Polymer Laboratory)
Developing solvent: dimethylformamide
Flow rate: 0.7 ml/min
Column temperature: 65° C.
Detector: RI
Sample amount: 1 mg/g, 100 µl
The molecular weight is a peak top molecular weight Mp.

Example 1

Synthesis of Polyoxyethylene Derivative (p2)
(case where $L^1$=—$CH_2CH_2$—NHCO—$CH_2CH_2$—, X=maleimido group, a=1, and molecular weight=about 20,000)

Example 1-1: Synthesis of 2,3,4,5-dibenzylidene xylitol

In a reactor equipped with a thermometer, a nitrogen inlet tube and a stirrer were placed 150 g of xylitol and 3700 g of 6M sulfuric acid, and the xylitol was dissolved at room temperature. After adding 315 g of benzaldehyde, the mixture was heated at about 30° C. and continued to stir, thereby depositing crystals. The stirring was continued as it was for 6 hours or more. To the mixture was added 4.5 L of cooled distilled water, and the deposit was collected by filtration. The crystals were suspended in 3 L of an aqueous ethanol solution, neutralized by adding 10 N aqueous sodium hydroxide solution and filtered. The crystals obtained were further subjected to suspension washing and filtration repeatedly using an aqueous ethanol solution, a mixed solution of ethanol and methyl tert-butyl ether (MTBE), and MTBE in order, and then dried under a reduced pressure to obtain 260 g of 2,3,4,5-dibenzylidene xylitol (molar yield: 85%).

$^1$H-NMR (CDCl$_3$, internal standard TMS) δ (ppm):
3.80-4.40 (7H, m, —CH$_2$—O—, —CH—O—),
5.59 (1H, s, Ph-CH—O—),
5.67 (1H, s, Ph-CH—O—),
7.30-7.65 (10H, m, Ph-CH—O—)

Example 1-2: Synthesis of α-(2,3,4,5-dibenzylidene xylitol) ω-hydroxypolyoxyethylene (Molecular Weight=about 20,000)

In an autoclave were charged 50 g (0.15 mol) of 2,3,4,5-dibenzylidene xylitol, 2000 g of dehydrated toluene and 3.8 g of a 28% methanol solution of sodium methoxide. After the inside of the system was replaced by nitrogen, the temperature was raised to 50° C. and toluene and methanol were distilled off under a reduced pressure. Further, 1000 g of dehydrated toluene was added and distilled off under a reduced pressure. After 2950 g (67 mol) of ethylene oxide was added at a pressure of 1 MPa or lower at 100 to 150° C., the reaction was continued for 1 hour. After unreacted ethylene oxide gas was removed under a reduced pressure, 2800 g of the desired compound was obtained (molar yield: 90%).

$^1$H-NMR (CDCl$_3$, internal standard TMS) δ (ppm):
3.40-3.90 (about 1880H, m, —CH$_2$O(CH$_2$CH$_2$O)$_m$H),
5.59 (1H, s, Ph-CH—O—),
5.67 (1H, s, Ph-CH—O—),
7.30-7.65 (10H, m, Ph-CH—O—)
Molecular weight (GPC/Mp): 20644 (m=about 469)

Example 1-3: Synthesis of α-(2,3,4,5-dibenzylidene xylitol) ω-amine polyoxyethylene (Molecular Weight=about 20,000)

In a four-necked flask equipped with a thermometer, a nitrogen inlet tube, a stirrer, a Dean-Stark tube and a condenser tube were placed 200 g (10 mmol) of α-(2,3,4,5-dibenzylidene xylitol) ω-hydroxy polyoxyethylene and 600 g of toluene, and the mixture was heated to 60° C. and dissolved with stirring and introduction of nitrogen. The temperature was raised to 110° C. and about 300 g of a fraction was taken out as an azeotrope with toluene to perform dehydration. After cooling to 40° C., 1.0 kg of dehydrated acetonitrile was added and 2.2 g (15 mmol) of phthalimide and 3.9 g (15 mmol) of triphenylphosphine were added. Then, 3.0 g (15 mmol) of diisopropyl azodicarboxylate was added, followed by the reaction at room temperature for 2 hours.

After the reaction, the solvent was distilled off under a reduced pressure and 400 g of methanol and 30 g (0.5 mol) of ethylenediamine were added, followed by the reaction at 60° C. for 4 hours. The mixture was diluted with 1.0 kg of dichloromethane and extraction was performed twice with 500 g of a 25% aqueous sodium chloride solution. About 1.5 kg of a fraction was taken out at 40° C. under a slightly reduced pressure, the mixture was cooled to room temperature, 600 g of ethyl acetate was added thereto, and magnesium sulfate was added to perform dehydration. After the magnesium sulfate was removed by filtration, 600 g of n-hexane was added to the filtrate to crystallize. After the crystals were collected by filtration, they were dissolved in 800 g of ethyl acetate at 40° C. and, after cooling to room temperature, 600 g of n-hexane was added thereto to crystallize. The crystals collected by filtration were washed with 1.0 kg of n-hexane. The crystals were collected by filtration and dried under vacuum to obtain 184 g of α-(2,3,4,5-dibenzylidene xylitol) ω-amine polyoxyethylene (molar yield: 92%).

$^1$H-NMR (CDCl$_3$, internal standard TMS) δ (ppm):
2.85-2.92 (2H, t, —CH$_2$—NH$_2$),
3.40-3.90 (about 1880H, m, —CH$_2$O(CH$_2$CH$_2$O)$_m$—CH$_2$O—),
5.59 (1H, s, Ph-CH—O—),
5.67 (1H, s, Ph-CH—O—),
7.30-7.65 (10H, m, Ph-CH—O—)

Example 1-4-1: Synthesis of Compound (p1) α-xylitol ω-amine polyoxyethylene (Molecular Weight=about 20,000) (Deprotection Step Using Acid)

In a 3-L three-necked flask equipped with a thermometer and a stirrer were placed 100 g (5 mmol) of α-(2,3,4,5-dibenzylidene xylitol) ω-amine polyoxyethylene and 1.8 kg of ion-exchange water, and the mixture was dissolved with stirring and introduction of nitrogen. Phosphoric acid (85%) was dropwise added so as to be pH 1.40 and the reaction was performed at room temperature for 8 hours.

After the reaction, the mixture was neutralized by adding a 10N aqueous sodium hydroxide solution, and after the addition of 360 g of sodium chloride, the pH was adjusted to 12.0 by further adding a 10N aqueous sodium hydroxide solution. Thereto was added 500 g of toluene, followed by extraction twice at 50° C. The solvent was removed under a reduced pressure, 500 g of ethyl acetate was added, and magnesium sulfate was added to perform dehydration. After separating the magnesium sulfate by filtration, 400 g of n-hexane was added to the filtrate to crystallize. The crystals collected by filtration were washed with 400 of n-hexane. The crystals were collected by filtration and dried under vacuum to obtain 90 g of Compound (p1) (molar yield: 90%).

$^1$H-NMR (D$_2$O) δ (ppm):
2.84-2.88 (2H, t, —CH$_2$—NH$_2$),
3.40-3.90 (about 1880H, m, —CH$_2$O(CH$_2$CH$_2$O)$_m$—CH$_2$—)

Example 1-4-2: Synthesis of Compound (p1) α-xylitol ω-amine polyoxyethylene (Molecular Weight=about 20,000) (Deprotection Step Using Reduction Reaction)

Into a 500-mL three-necked flask equipped with a thermometer and a stirrer were charged 40 g (1.0 mmol) of α-(2,3,4,5-dibenzylidene xylitol) ω-amine polyoxyethylene and 20 g of 5% palladium carbon (50% hydrous product). After replacement by nitrogen, 400 mL of methanol and 67 mL of cyclohexene were added thereto and the mixture was heated and gently refluxed at 52 to 55° C. to perform the reaction for 3 hours. After cooling to room temperature, the palladium carbon was removed by filtration and the filtrate was concentrated. Then, 350 g of toluene and 250 g of n-hexane were added to the concentrate to crystallize. The crystals collected by filtration were washed with 200 g of n-hexane. The crystals were collected by filtration and dried under vacuum to obtain 36 g of Compound (p1) (molar yield: 90%).

$^1$H-NMR (D$_2$O) δ (ppm):
2.84-2.88 (2H, t, —CH2-NH2),
3.40-3.90 (about 1880H, m, —CH$_2$O(CH$_2$CH$_2$O)$_m$—CH$_2$—)

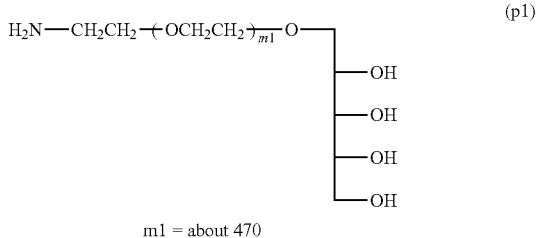

m1 = about 470

Example 1-5: Synthesis of α-xylitol ω-maleimide polyoxyethylene (Molecular Weight=about 20,000)

Into a 100-mL four-necked flask equipped with a thermometer, a nitrogen inlet tube, a stirrer and a condenser tube were charged 10 g (0.5 mmol) of Compound (p1) and 50 g of toluene, and the mixture was dissolved by heating at 40° C. After light shielding, 160 mg (0.6 mmol) of N-succinimidyl maleimido propionate was added and the reaction was performed at 40° C. for 4 hours.

After the reaction, filtration was performed and 30 g of ethyl acetate was added to dilute the filtrate, followed by addition of 40 g of n-hexane to crystallize. After the crystals were collected by filtration, they were dissolved in 100 g of ethyl acetate at 40° C. and, after cooling to room temperature, 50 g of n-hexane was added thereto to crystallize. The dissolution of the crystals and the crystallization step were further repeated once. The crystals collected by filtration were washed with 50 g of n-hexane. The crystals were collected by filtration and dried under vacuum to obtain 9 g of Compound (p2) shown below (molar yield: 90%).

$^1$H-NMR (CDCl$_3$, internal standard TMS) δ (ppm):
2.49-2.54 (2H, t, —NHCOC$\underline{H}_2$CH$_2$—),
3.40-3.90 (about 1880H, m, —C$\underline{H}_2$O(C$\underline{H}_2$C$\underline{H}_2$O)$_m$—C$\underline{H}_2$—, —C$\underline{H}_2$NHCO—),
6.70 (2H, s, —C$\underline{H}$=C$\underline{H}$—)

NMR Purity:

Percentage obtained by dividing a peak integration value 1.86 derived from a maleimido group at 6.70 (ppm) when a peak integration value derived from a PEG chain at 3.40-3.90 (ppm) is taken as 1880 by a theoretical value 2

1.86/2×100=93%   NMR purity of Compound (p2):

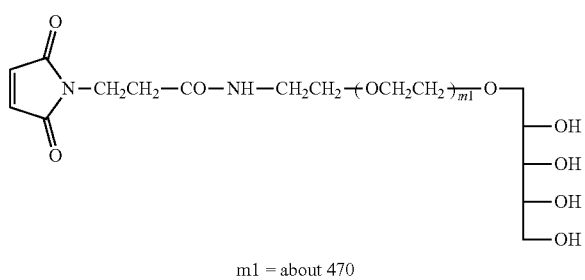

m1 = about 470

Example 2

Synthesis of Polyoxyethylene Derivative (p3)
(case where L$^1$=—CH$_2$CH$_2$—, X=p-nitrophenyl carbonate group, a=1, and molecular weight=about 5,000)

Example 2-1: Synthesis of α-(2,3,4,5-dibenzylidene xylitol) ω-hydroxy polyoxyethylene (Molecular Weight=about 5,000)

In an autoclave were charged 100 g (0.30 mol) of 2,3,4,5-dibenzylidene xylitol, 2000 g of dehydrated toluene and 2.0 g of a 28% methanol solution of sodium methoxide. After the inside of the system was replaced by nitrogen, the temperature was raised to 50° C. and toluene and methanol were distilled off under a reduced pressure. Further, 1000 g of dehydrated toluene was added and distilled off under a reduced pressure. Then, 1410 g (32 mol) of ethylene oxide was added at a pressure of 1 MPa or lower at 100 to 150° C. The reaction was continued for 1 hour and after unreacted ethylene oxide gas was removed under a reduced pressure, 1450 g of the desired compound was obtained (molar yield: 92%).

$^1$H-NMR (CDCl$_3$, internal standard TMS) δ (ppm):
3.40-3.90 (about 480H, m, —C$\underline{H}_2$O(C$\underline{H}_2$C$\underline{H}_2$O)$_m$H),
5.59 (1H, s, Ph-C$\underline{H}$—O—),
5.67 (1H, s, Ph-C$\underline{H}$—O—),
7.30-7.65 (10H, m, $\underline{Ph}$-CH—O—)
Molecular weight (GPC/Mp): 5,244 (m=about 119)

Example 2-2: Synthesis of α-xylitol ω-p-nitrophenylcarbonato polyoxyethylene (Molecular Weight=about 5,000)

In a four-necked flask equipped with a thermometer, a nitrogen inlet tube, a stirrer, a Dean-Stark tube and a condenser tube were placed 50 g (10 mmol) of α-(2,3,4,5-dibenzylidene xylitol) ω-hydroxy polyoxyethylene and 250 g of toluene, and the mixture was heated to 60° C. and dissolved with stirring and introduction of nitrogen. The temperature was raised to 110° C. and about 50 g of a fraction was taken out as an azeotrope with toluene to perform dehydration. After cooling to 60° C., 1.5 g (15.0 mmol) of triethylamine and 2.5 g (12.5 mmol) of p-nitrophenyl chloroformate were added, followed by the reaction at 60° C. for 6 hours.

Then, 250 g of an aqueous phosphoric solution having pH of 1.40 was added, followed by the reaction at room temperature for 8 hours. After the reaction, the toluene layer was removed, and a 10N aqueous sodium hydroxide solution was added to neutralize. After the addition of 360 g of sodium chloride, 500 g of chloroform was added, and extraction was performed twice at room temperature. The solvent was removed under a reduced pressure, 500 g of ethyl acetate was added, and magnesium sulfate was added to perform dehydration. After separating the magnesium sulfate by filtration, 400 g of n-hexane was added to the filtrate to crystallize. The crystals collected by filtration were washed with 400 of n-hexane. The crystals were collected by filtration and dried under vacuum to obtain 45 g of Compound (p3) (molar yield: 90%).

$^1$H-NMR (CDCl$_3$, internal standard TMS) δ (ppm):
3.40-3.90 (about 480H, m, —C$\underline{H}_2$O(C$\underline{H}_2$C$\underline{H}_2$O)$_m$C$\underline{H}_2$—O—),
4.40-4.50 (2H, m, —C$\underline{H}_2$—O—CO—O-Ph-NO$_2$),
7.39 (2H, d, $\underline{Ph}$-NO$_2$),
8.28 (2H, d, $\underline{Ph}$-NO$_2$)

NMR Purity:

Percentage obtained by dividing a peak integration value 1.9 derived from a methylene group bonded to a p-nitrophenyl carbonate group at 4.40-4.50 (ppm) when a peak integration value derived from a PEG chain at 3.40-3.90 (ppm) is taken as 480 by a theoretical value 2

1.9/2×100=95%

NMR purity of Compound (p3):

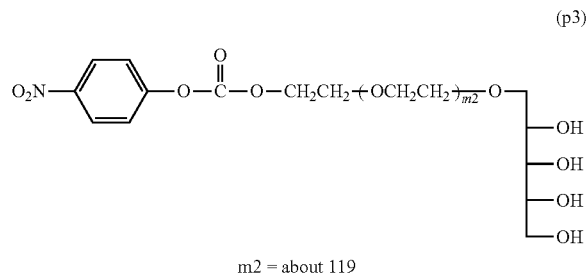

m2 = about 119

Comparative Example 1

Synthesis of Polyoxyethylene derivative (p2) was performed according to the production method described in Patent Document 1.

(case where $L^1$=—$CH_2CH_2$—NHCO—$CH_2CH_2$—, X=maleimido group, a=1, and molecular weight=about 20,000)

Comparative Example 1-1: Synthesis of diisopropylidenexylitol: Compounds (p4) and (p5)

In a 5-L round-bottom flask equipped with a thermometer, a nitrogen inlet tube and a stirrer were placed 1000 g of xylitol, 1916 g of 2,2-dimethoxypropane and 37.5 mg of p-toluenesulfonic acid monohydrate and the reaction was performed at 65° C. with introduction of nitrogen thereinto. The solvent of the reaction solution was distilled off and purification by distillation (b.p. 108° C./0.15 mmHg) was performed to obtain 1527 g of an isomer mixture of 1,2,3,4-diisopropylidenexylitol (formula (p4)) and 1,2,4,5-diisopropylidenexylitol (formula (p5)) (molar yield: 95%).

$^1$H-NMR (CDCl$_3$, internal standard TMS) δ (ppm):
1.37-1.44 (12H, m, —C(C$\underline{H}_3$)$_2$),
3.59-3.65 (1H, m, —C$\underline{H}$—O—),
3.81-3.90 (2H, m, —C$\underline{H}_2$—O—),
3.98-4.01 (1H, m, —C$\underline{H}$—O—),
4.04-4.10 (2H, m, —C$\underline{H}_2$—O—),
4.11-4.23 (1H, m, —C$\underline{H}$—O—)

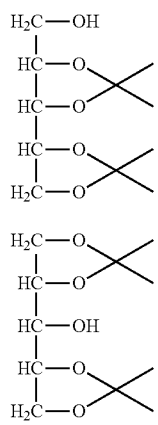

Comparative Example 1-2: Synthesis of 1,2,3,4-diisopropylidene-5-(tert-butyldiphenylsilyl)xylitol: Compound (p6)

In a 2-L round-bottom flask equipped with a thermometer, a nitrogen inlet tube and a stirrer were placed 250 g of diisopropylidenexylitol (isomer mixture) purified in 1-1, 1000 g of dichloromethane, 26 g of 4-dimethylaminopyridine and 109 g of triethylamine, and the mixture was dissolved at room temperature with introduction of nitrogen thereinto. After cooling to 10° C. or lower, 297 g of tert-butylchlorodiphenylsilane was dropwise added thereto. After the dropwise addition, the temperature was returned to room temperature and, after the reaction for 2 hours, an aqueous saturated sodium hydrogen carbonate solution was added to wash. After dehydration over magnesium sulfate, the solvent was distilled off, and 1,2,4,5-diisopropylidenexylitol was removed at 135° C. under a reduced pressure (0.2 mmHg) to obtain 200 g of 1,2,3,4-diisopropylidene-5-(tert-butyldiphenylsilyl)xylitol (formula (p6)) (molar yield: 40%).

$^1$H-NMR (CDCl$_3$, internal standard TMS) δ (ppm):
1.06 (9H, m, —Si—C—(C$\underline{H}_3$)$_3$),
1.37, 1.42, 1.43 (12H, s, —O—C—C$\underline{H}_3$),
3.72-3.82 (1H, m, —C$\underline{H}$—O—, —C$\underline{H}_2$—O—),
3.95 (1H, dd, —C$\underline{H}$—O—),
3.99-4.06 (2H, m, —C$\underline{H}_2$O—),
4.11-4.15 (1H, m, —C$\underline{H}$—O—),
7.36-7.54 (6H, m, $\underline{Ph}$-Si(-$\underline{Ph}$)-O—),
7.66-7.70 (4H, m, $\underline{Ph}$-Si(-$\underline{Ph}$)-O—)

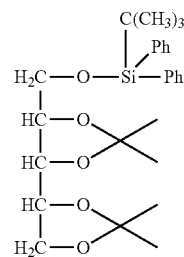

Comparative Example 1-3: Synthesis of 1,2,3,4-diisopropylidenexylitol: Compound (p4)

In a 2-L round-bottom flask equipped with a thermometer, a nitrogen inlet tube and a stirrer were placed 500 g of 1,2,3,4-diisopropylidene-5-(tert-butyldiphenylsilyl)xylitol and 440 g of dehydrated tetrahydrofuran, and the mixture was homogenized at room temperature with introduction of nitrogen thereinto. After cooling to 20° C. or lower, 1270 ml of tetrabutylammonium fluoride (1 mol/L tetrahydrofuran solution) was dropwise added thereto. After the dropwise addition, the temperature was returned to room temperature, and after the reaction for 2 hours, the solvent was distilled off under a reduced pressure. The residue was dissolved in 2000 g of ethyl acetate and then the ethyl acetate layer was washed with purified water. After dehydration over magnesium sulfate, the solvent was distilled off, and 250 g of 1,2,3,4-diisopropylidenexylitol (formula (p4)) was obtain by column chromatography using chloroform and methanol as solvents and silica gel as a filler (molar yield: 60%).

$^1$H-NMR (CDCl$_3$, internal standard TMS) δ (ppm):
1.39, 1.44 (12H, s, —C$\underline{H}_3$), 3.62 (1H, dd, —C$\underline{H}$—O—),
3.08-3.89 (2H, m, —C$\underline{H}_2$—O—),
3.98-4.08 (1H, m, —C$\underline{H}$—O—, 2H, m, —C$\underline{H}_2$—O—),
4.18-4.23 (1H, m, —C$\underline{H}$—O—)

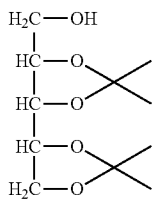

(p4)

Comparative Example 1-4: Synthesis of α-diisopropylidenexylitol polyoxyethylene (molecular weight: 20,000): Compound (p7)

Into an autoclave were charged 10 g (0.043 mol) of 1,2,3,4-diisopropylidenexylitol (5), 200 g of dehydrated toluene and 1.08 g of a 28% methanol solution of sodium methoxide. After the inside of the system was replaced by nitrogen, the temperature was raised to 50° C. and toluene and methanol were distilled off under a reduced pressure. After 840 g (19.1 mol) of ethylene oxide was added at a pressure of 1 MPa or lower at 100 to 150° C., the reaction was continued for another 1 hour. After unreacted ethylene oxide gas was removed under a reduced pressure, 770 g of Compound (p7) shown below was obtained (molar yield: 87%).

$^1$H-NMR (CDCl$_3$, internal standard TMS) δ (ppm):
1.37-1.44 (12H, m, —C(C$\underline{H}_3$)$_2$),
3.40-3.90 (about 1880H, m, —C$\underline{H}_2$O(C$\underline{H}_2$C$\underline{H}_2$O)$_m$H)
Molecular weight (GPC/Mp): 20,678 (m=about 470)

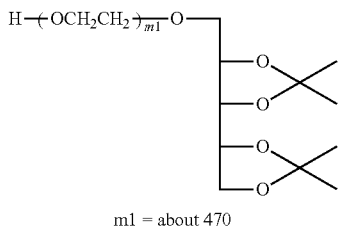

(p7)

m1 = about 470

Comparative Example 1-5: Synthesis of α-diisopropylidenexylitol ω-amine polyoxyethylene (Molecular Weight: 20,000): Compound (p8)

Into a 1-L four-necked flask equipped with a thermometer, a nitrogen inlet tube, a stirrer, a Dean-Stark tube and a condenser tube were charged 200 g (10 mmol) of α-diisopropylidenexylitol polyoxyethylene (p1) and 600 g of toluene, and the mixture was heated to 60° C. and dissolved with stirring and introduction of nitrogen. The temperature was raised to 110° C. and about 300 g of a fraction was taken out as an azeotrope with toluene to perform dehydration. After cooling to 40° C., 1.0 kg of dehydrated acetonitrile was added, and 2.2 g (15 mmol) of phthalimide and 3.9 g (15 mmol) of triphenylphosphine were added. Thereafter, 3.0 g (15 mmol) of diisopropyl azodicarboxylate was added, followed by the reaction at room temperature for 2 hours.

After the reaction, the solvent was distilled off under a reduced pressure and 400 g of methanol and 30 g (0.5 mol) of ethylenediamine were added, followed by the reaction at 60° C. for 4 hours. The mixture was diluted with 1.0 kg of dichloromethane and extraction was performed twice with 500 g of a 25% aqueous sodium chloride solution. About 1.5 kg of a fraction was taken out at 40° C. under a slightly reduced pressure, then cooling was performed to room temperature, 600 g of ethyl acetate was added thereto, and magnesium sulfate was added to perform dehydration. After the magnesium sulfate was removed by filtration, 600 g of n-hexane was added to the filtrate to crystallize. After the crystals were collected by filtration, they were dissolved in 800 g of ethyl acetate at 40° C. and, after cooling to room temperature, 600 g of n-hexane was added thereto to crystallize. The crystals collected by filtration were washed with 1.0 kg of n-hexane. The crystals were collected by filtration and dried under vacuum to obtain 184 g of Compound (p8) shown below (molar yield: 92%).

$^1$H-NMR (D$_2$O) δ (ppm):
1.37-1.44 (12H, m, —C(C$\underline{H}_3$)$_2$),
2.84-2.88 (2H, t, —C$\underline{H}_2$—NH$_2$),
3.40-3.90 (about 1880H, m, —C$\underline{H}_2$O(C$\underline{H}_2$C$\underline{H}_2$O)$_m$—C$\underline{H}_2$O—)

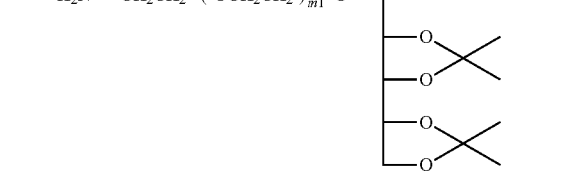

(p8)

m1 = about 470

Comparative Example 1-6: Synthesis of α-xylitol ω-amine polyoxyethylene (Molecular Weight: 20,000): Compound (p1)

Into a 3-L three-necked flask equipped with a thermometer and a stirrer were charged 100 g (5 mmol) of α-diisopropylidenexylitol ω-amine polyoxyethylene (p8) and 1.8 kg of ion-exchange water, and the mixture was dissolved with stirring and introduction of nitrogen. Phosphoric acid (85%) was dropwise added so as to be pH 1.40 and the reaction was performed at room temperature for 8 hours.

After the reaction, the mixture was neutralized by adding a 10N aqueous sodium hydroxide solution, and after the addition of 360 g of sodium chloride, was adjusted to pH 12.0 by further adding a 10N aqueous sodium hydroxide solution. Thereto was added 500 g of toluene, followed by extraction twice at 50° C. The solvent was distilled off under a reduced pressure, 500 g of ethyl acetate was added, and magnesium sulfate was added to perform dehydration. After the magnesium sulfate was removed by filtration, 400 g of n-hexane was added to the filtrate to crystallize. The crystals collected by filtration were washed with 400 of n-hexane. The crystals were collected by filtration and dried under vacuum to obtain 90 g of Compound (p1) shown below (molar yield: 90%).

$^1$H-NMR (D$_2$O) δ (ppm):
2.84-2.88 (2H, t, —C$\underline{H}$2-NH2), 3.40-3.90 (about 1880H, m, —C$\underline{H}_2$O(C$\underline{H}_2$C$\underline{H}_2$O)$_m$—C$\underline{H}_2$—)

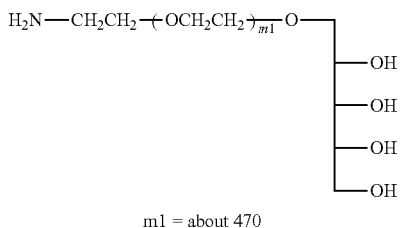

(p1)

m1 = about 470

Comparative Example 1-7: Synthesis of α-xylitol ω-maleimide polyoxyethylene (Molecular Weight: 20,000): Compound (p2)

Into a 50-mL four-necked flask equipped with a thermometer, a nitrogen inlet tube, a stirrer and a condenser tube were charged 5 g (0.25 mmol) of α-xylitol ω-amine polyoxyethylene (p3) and 50 g of toluene, and the mixture was dissolved by heating at 40° C. After light shielding, 80 mg (0.3 mmol) of N-succinimidyl maleimido propionate was added and the reaction was performed at 40° C. for 4 hours.

After the reaction, filtration was performed, and 15 g of ethyl acetate was added to dilute the filtrate, followed by addition of 20 g of n-hexane to crystallize. After the crystals were collected by filtration, they were dissolved in 50 g of ethyl acetate at 40° C. and, after cooling to room temperature, 25 g of n-hexane was added thereto to crystallize. The dissolution of the crystals and the crystallization step were further repeated once. The crystals collected by filtration were washed with 25 g of n-hexane. The crystals were collected by filtration and dried under vacuum to obtain 4.5 g of Compound (p2) shown below (molar yield: 90%).

$^1$H-NMR (CDCl$_3$, internal standard TMS) δ (ppm):
2.49-2.54 (2H, t, —NHCOC$\underline{H}_2$CH$_2$—),
3.40-3.90 (about 1880H, m, —C$\underline{H}_2$O(C$\underline{H}_2$C$\underline{H}_2$O)$_m$—C$\underline{H}_2$—, —C$\underline{H}_2$NHCO—)
6.70 (2H, s, —C$\underline{H}$=C$\underline{H}$—)

NMR Purity:
Percentage obtained by dividing a peak integration value 1.86 derived from a maleimido group at 6.70 (ppm) when a peak integration value derived from a PEG chain at 3.40-3.90 (ppm) is taken as 1880 by a theoretical value 2

1.86/2×100=93%    NMR purity of Compound (p2):

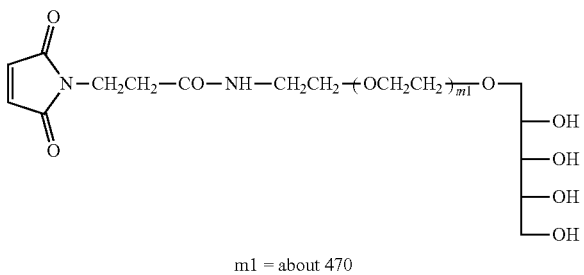

(p2)

m1 = about 470

(Comparison of Total Molar Yield Depending on Production Method of Polyoxyethylene Derivative (p2))

The total molar yields of the polyoxyethylene derivative obtained according to the invention and the polyoxyethylene derivative obtained under the conditions described in Patent Document 1 (JP-A-2012-214747) are summarized in Table 1 and Table 2.

TABLE 1

| Step | Example | | | | |
|---|---|---|---|---|---|
| | 1-1 | 1-2 | 1-3 | 1-4 | 1-5 |
| Total Molar Yield | 85% | 77% | 70% | 63% | 57% |

Total molar yield: the product of yields of respective steps

TABLE 2

| | Comparative Example (Patent Document 1: JP-A-2012-214747) | | | | | | |
|---|---|---|---|---|---|---|---|
| | Step | | | | | | |
| | 1-1 | 1-2 | 1-3 | 1-4 | 1-5 | 1-6 | 1-7 |
| Total Molar Yield | 95% | 38% | 23% | 20% | 18% | 16% | 15% |

Total molar yield: the product of yields of respective steps

In the production method described in Patent Document 1, a large decrease in the yield was recognized because three steps were required for obtaining the protected product of xylitol, the column chromatography was used in the purification step, and the like. On the other hand, in the production method according to the invention, the protected product of xylitol could obtain in one step and the special purification step was not required so that the total molar yield could be greatly improved. Further, as to the purity of the final polyoxyethylene derivative, the equivalent quality could be obtained.

While the invention has been described in detail and with reference to specific embodiments thereof, it will be apparent to those skilled in the art that various changes and modifications can be made therein without departing from the spirit and scope of the invention.

This present application is based on Japanese patent application filed on Mar. 31, 2017 (Japanese Patent Application No. 2017-069699), and the whole contents thereof are incorporated herein by reference. Also, all the references cited herein are incorporated as a whole.

The invention claimed is:

1. A production method of a polyoxyethylene derivative represented by the following formula (1) which comprises performing the following step (A), step (B), step (C) and step (D):

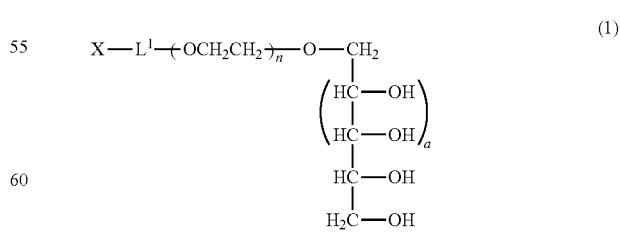

(1)

(in the formula (1), L$^1$ is a divalent linker, X is a functional group capable of reacting with a physiologically active substance, a is 1 or 2, and n is from 11 to 3,650);

Step (A): a step wherein in a polyhydric alcohol having 5 or 7 hydroxyl groups, 4 or 6 hydroxyl groups are protected by cyclic benzylidene acetalization to obtain a compound having the hydroxyl group at a 1-position and a protective group of a cyclic benzylidene acetal structure;

Step (B): a step wherein from 11 to 3,650 moles of ethylene oxide are polymerized to the compound obtained in the step (A) to obtain a polyoxyethylene derivative;

Step (C): a step wherein the hydroxyl group at a terminal of the polyoxyethylene derivative obtained in the step (B) is converted to the functional group capable of reacting with a physiologically active substance; and Step (D): a step wherein the protective group of the polyoxyethylene derivative is deprotected.

2. The method as claimed in claim 1, wherein an acidic solution is used as a solvent in the step (A).

3. The method as claimed in claim 1, wherein the step (C) and the step (D) are performed in succession.

4. The method as claimed in claim 1, wherein the step (D) is performed under acidic conditions.

5. The method as claimed in claim 1, wherein the step (D) is performed by a reduction reaction.

6. The method as claimed in claim 2, wherein the step (C) and the step (D) are performed in succession.

* * * * *